(12) United States Patent
Krueger et al.

(10) Patent No.: US 7,326,311 B2
(45) Date of Patent: Feb. 5, 2008

(54) METHOD OF PRODUCING INTERMITTENTLY ELASTIC WEBS

(75) Inventors: Gary A. Krueger, Neenah, WI (US);
John T. Hahn, Merrill, WI (US);
Eric-John R. Gilgenbach, Winneconne, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 347 days.

(21) Appl. No.: 11/117,900

(22) Filed: Apr. 29, 2005

(65) Prior Publication Data

US 2006/0243373 A1 Nov. 2, 2006

(51) Int. Cl.
*B32B 37/00* (2006.01)
*A61F 13/15* (2006.01)

(52) U.S. Cl. .............. 156/164; 156/163; 156/229; 156/256; 156/259; 156/267; 156/271

(58) Field of Classification Search .......... 156/160, 156/163, 164, 229, 256, 264, 265, 259, 267, 156/271
See application file for complete search history.

(56) References Cited

U.S. PATENT DOCUMENTS

| | | | |
|---|---|---|---|
| 4,798,603 A | 1/1989 | Meyer et al. | |
| 4,846,823 A * | 7/1989 | Enloe | 604/385.28 |
| 5,034,007 A | 7/1991 | Igaue et al. | |
| 5,110,386 A | 5/1992 | Ochi et al. | |
| 5,226,992 A | 7/1993 | Morman | |
| 5,330,598 A | 7/1994 | Erdman et al. | |
| 5,439,459 A | 8/1995 | Tanji et al. | |
| 5,540,672 A * | 7/1996 | Roessler et al. | 604/385.26 |
| 5,827,387 A | 10/1998 | Reynolds et al. | |
| 5,985,081 A | 11/1999 | Reynolds | |
| 6,056,733 A | 5/2000 | Kielpikowski | |
| 6,264,641 B1 | 7/2001 | Van Gompel et al. | |
| 6,322,547 B1 | 11/2001 | Hansson | |
| 6,346,162 B1 | 2/2002 | Reynolds et al. | |

FOREIGN PATENT DOCUMENTS

| | | |
|---|---|---|
| EP | 0 539 703 B1 | 3/1997 |
| JP | 03-286761 A | 12/1991 |
| WO | WO 98/29251 A1 | 7/1998 |

\* cited by examiner

*Primary Examiner*—Jeff H. Aftergut
(74) *Attorney, Agent, or Firm*—David J. Klann; David J. Arteman

(57) ABSTRACT

A method of producing an intermittently elastic web. The method includes providing a first longitudinally extending web having a first lateral edge, a second lateral edge and an intermediate portion located between the first and second lateral edges. The method also includes joining a first elastic element to the intermediate portion in a longitudinally extending wave shape, the wave shape having wave crests and wave troughs.

20 Claims, 11 Drawing Sheets

METHOD OF PRODUCING INTERMITTENTLY ELASTIC WEBS

BACKGROUND

Absorbent articles such as infant diapers, training pants, sanitary napkins, adult incontinence products and the like are well known. Such articles have achieved a wide acceptance due to their ability to absorb body exudates without leaking. In order to achieve a high degree of leakage protection, it has become increasingly common to rely on systems wherein numerous components cooperate. For example, in the case of infant diapers, urine is generally absorbed by an absorbent core comprising a matrix of wood pulp fluff and superabsorbent material. Such an absorbent core is known to be particularly well suited for absorbing and holding urine in a diaper structure. Unfortunately, it is not always possible for the absorbent core to absorb and hold urine at the rate at which it is delivered. Thus, it has become increasingly common to rely on various mechanical containment means to hold urine within the diaper until it can be absorbed and held by the absorbent core.

For example, it is well known to those skilled in the art to provide elasticized leg cuffs along the leg openings of a diaper. The leg cuffs are said to assist in the containment of body exudates. Similarly, it is well known to those skilled in the art to use waist elastics in a diaper to obtain a tighter seal about the waist of a wearer. The waist elastics also contribute to the mechanical containment of body exudates.

In an attempt to improve the mechanical containment of body exudates, it is also known to employ a pair of containment flaps along the longitudinal sides of absorbent articles such as infant diapers, training pants, sanitary napkins, adult incontinence products and the like. The containment flaps are generally thought to be particularly well suited for the containment of fecal matter and the prevention of lateral flow of liquid waste until the liquid waste can be absorbed by the absorbent article. Elasticized leg cuffs are often used in conjunction with the containment flaps to help contain body exudates. Further, the shape of the user's legs in relation to the product has shown that elasticized leg cuffs that are curved may provide benefits in containment as well as comfort of the product.

Absorbent articles are generally produced in a continuous process, in which a web of material, that normally forms the backsheet or other layer of the article, travels continuously through the process line in successive stages, which include the application of absorbent bodies and the application of further surface sheets or layers and elastic elements. The individual articles are cut from the continuous composite web in the final stages of such a process. The elastic elements are most often mounted in a pre-stretched state, i.e. have been stretched from a rest state to which they strive to return. So that the pre-stretched elastic elements will not contract and therewith gather together or pucker the material to which they are fastened, the elastic elements are maintained in a stretched state until the final stages of the manufacturing process. This can be readily achieved with elastic elements that extend the full length of the article in the movement direction of the process line. However, in the case of elastic elements that are active over only a part of the length of the article in the movement direction, a problem arises in retaining the elements in a pre-stretched state without complicating the process and/or without mounting functionally inactive parts of elastic elements on the web in the article manufacturing process.

Accordingly, there is a need for a process for making curved intermittent elastics that are aesthetically pleasing and can be applied in a high-speed application.

SUMMARY

In response to the foregoing need, the present inventor undertook intensive research and development efforts that resulted in the discovery of a method for producing an intermittently elastic web. One version of the present invention includes a method of producing an intermittently elastic web, including providing a first longitudinally extending web having a first lateral edge, a second lateral edge and an intermediate portion located between the first and second lateral edges. The method also includes joining a first elastic element to the intermediate portion in a longitudinally extending wave shape, the wave shape having wave crests and wave troughs. The method further includes joining a second elastic element to the first longitudinally extending web adjacent the first lateral edge; and joining a third elastic element to the first longitudinally extending web adjacent the second lateral edge. The method further includes cutting the web longitudinally to form a first and second intermittently elastic web comprising cut portions of the first elastic element.

Another version of the present invention provides a method of producing a disposable absorbent article, including providing an absorbent assembly comprising a liquid-impervious outer cover, a liquid pervious liner, and an absorbent core therebetween. The method includes providing a first longitudinally extending web having a first lateral edge, a second lateral edge and an intermediate portion located between the first and second lateral edges. The method also includes joining a first elastic element to the intermediate portion in a longitudinally extending wave shape, the wave shape having wave crests and wave troughs; joining a second elastic element to the first longitudinally extending web adjacent the first lateral edge; and joining a third elastic element to the first longitudinally extending web adjacent the second lateral edge. The method includes cutting the web longitudinally to form a first and second intermittently elastic webs comprising cut portions of the first elastic element. The method includes displacing the first and second intermittently elastic webs longitudinally in relation to each other so that the wave crests and wave troughs are substantially aligned in the longitudinal direction. The method includes joining the first intermittently elastic webs to the absorbent assembly, the first intermittently elastic webs joined at a location between the cut portions of the first elastic element and the second elastic element; and joining the second intermittently elastic webs to the absorbent assembly, the second intermittently elastic webs joined at a location between the cut portions of the first elastic element and the third elastic element.

Still another version of the present invention includes a method of producing a disposable absorbent article including providing an absorbent assembly comprising a liquid-impervious outer cover, a liquid pervious liner, and an absorbent core therebetween. The method includes providing a first longitudinally extending web having a first lateral edge, a second lateral edge and an intermediate portion located between the first and second lateral edges. The method includes joining a first elastic element to the intermediate portion in a longitudinally extending wave shape, the wave shape having wave crests and wave troughs; joining a second elastic element to the first longitudinally extending web adjacent the first lateral edge; and joining a third elastic element to the first longitudinally extending web adjacent the second lateral edge. The method includes cutting the web longitudinally to form a first and second intermittently elastic webs comprising cut portions of the first elastic element and a cut edge. The method includes removing portions of the first and second intermittently elastic web located between the cut portions of the first elastic element and the cut edge. The method includes displacing the first and second intermittently elastic webs longitudinally in relation to each other so that the wave crests and wave troughs are substantially aligned in the longitudinal direction. The method includes joining the first intermittently elastic webs to the absorbent assembly at a location between the cut portions of the first elastic element and the second elastic element. The method also includes joining the second intermittently elastic web to the absorbent assembly at a location between the cut portions of the first elastic element and the third elastic element.

DRAWINGS

The foregoing and other features, aspects and advantages of the present invention will become better understood with regard to the following description, appended claims and accompanying drawings, where:

Figure 6:
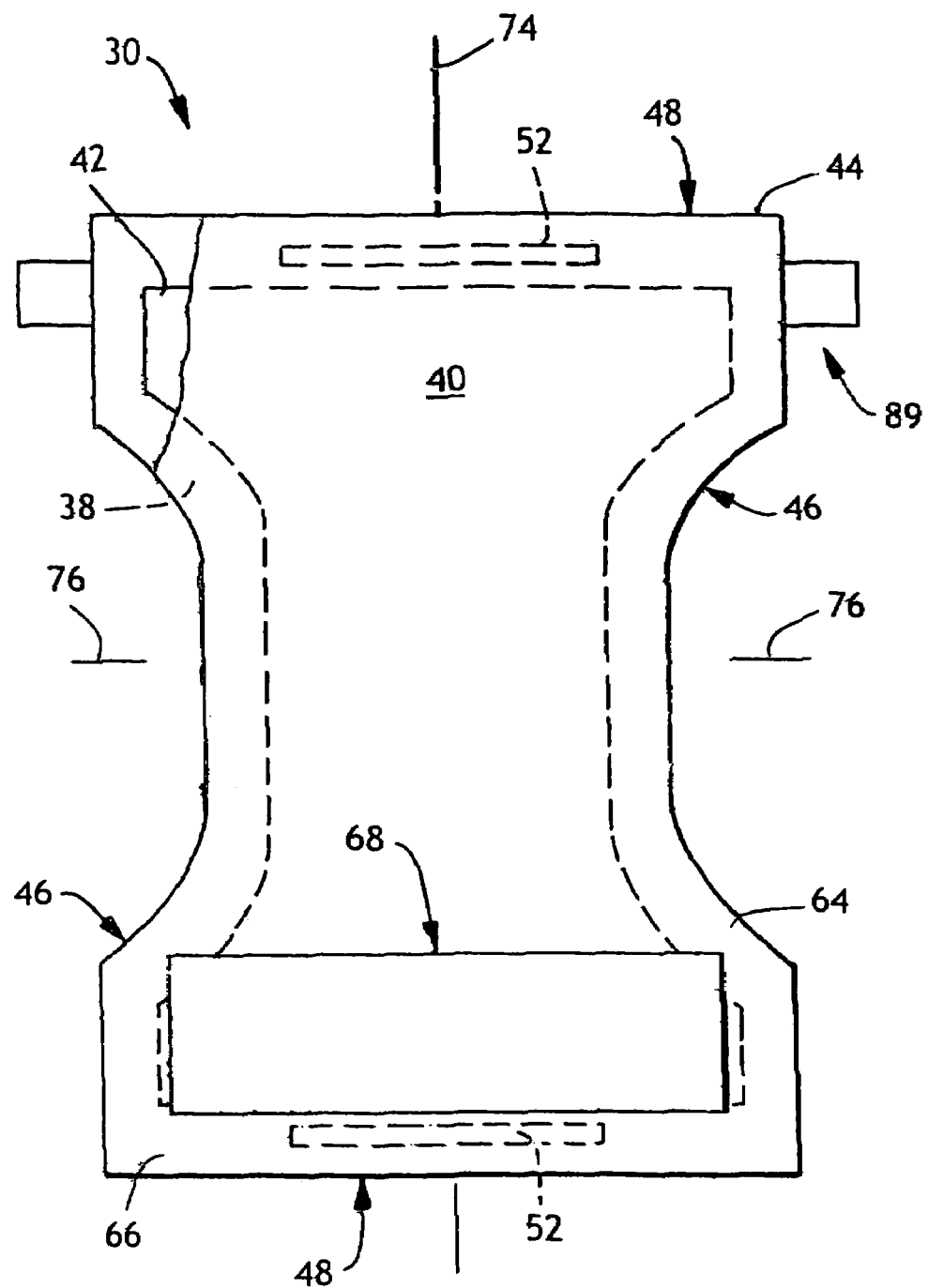
Figure 7:
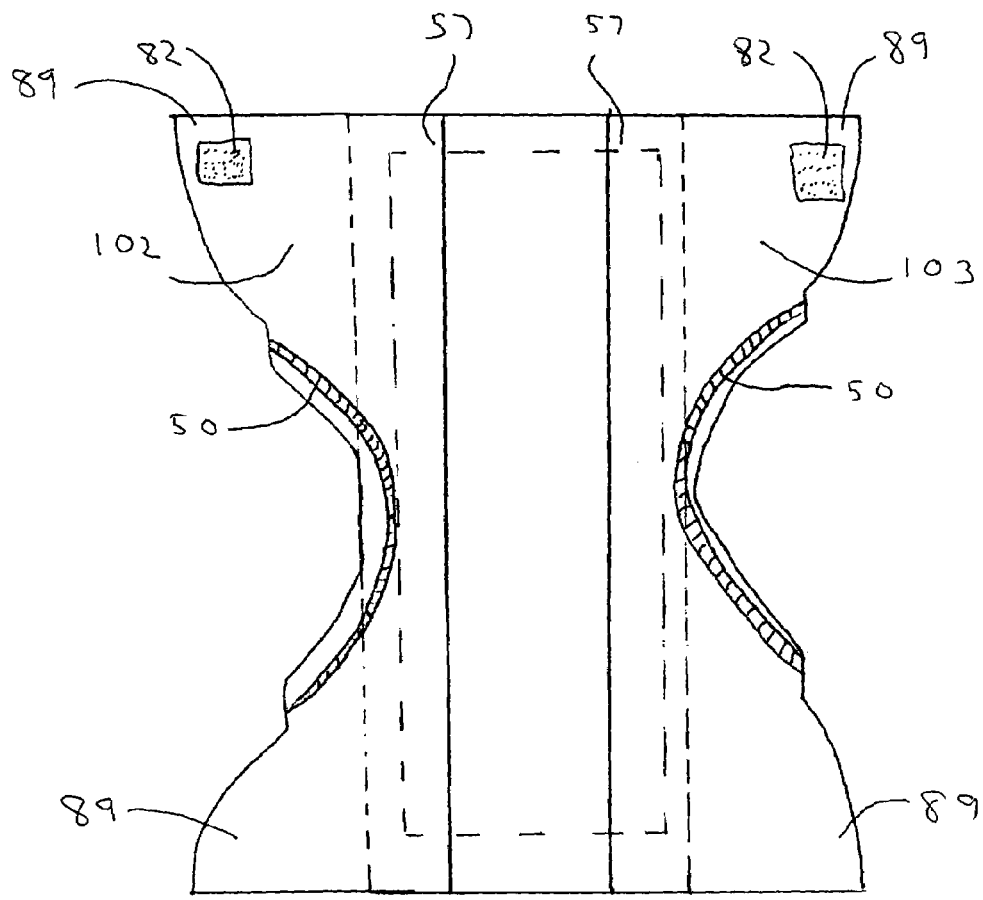

FIG. 6 illustrates a plan view of a disposable absorbent article in an unfolded, flat-out, uncontracted state, with the garment facing surface of the article facing the viewer and with portions of the article partially cut away to illustrate underlying features; and FIG. 7 illustrates a plan view of a second disposable absorbent article in an unfolded, flat-out, uncontracted state (i.e., with all elastic induced gathering and contraction removed).

DESCRIPTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

As used herein, the term "disposable" refers to articles which are intended to be discarded after a limited use and which are not intended to be laundered or otherwise restored for reuse. The disposable absorbent articles of the present invention will be described in terms of a disposable diaper which is adapted to be worn by infants about the lower torso. It is understood that the present invention is equally adaptable for use with other types of disposable absorbent articles such as adult incontinence garments, diaper-pants, children's training pants, surgical gowns and the like.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, reference to two materials or elements being "joined" is intended to refer to the situation wherein the two materials or elements are directly joined to one another or where they are indirectly joined to one another or where they are indirectly joined to an intermediate element. Similarly, methods of joining two materials or elements include forming the elements or materials integrally, or attaching the elements together such as through the use of adhesive bonds, sonic bonds, thermal bonds, pinning, stitching, or a variety of other attachment techniques known in the art, as well as combinations thereof.

"Stretchable", refers to materials which are either elastic or extensible, that is materials which when elongated in one or more dimensions either exert a force tending to move the material at least partially to its original dimensions (elastic), or which remain in the elongated configuration (extensible).

It should be noted that the stretch, elastic or extensible properties of a stretchable material are determined when the material is dry. Additionally, the percentage of elongation, extension or permanent deformation can be determined in accordance with the following formula:

$$100*[(L-Lo)/(Lo)]$$

where: L=elongated length; and
Lo=initial length.

Figure 1:
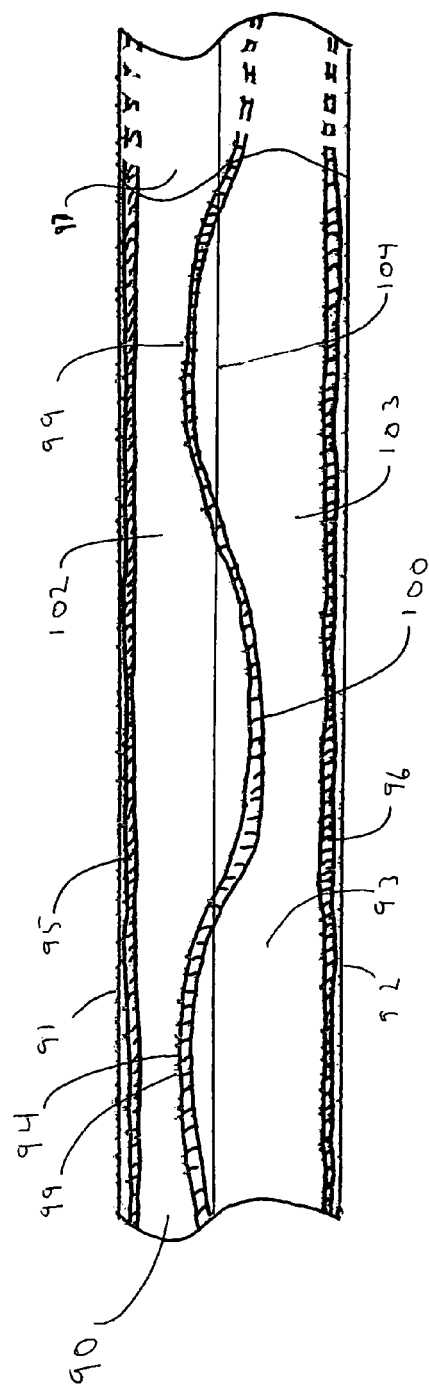
FIG. 1 illustrates a version of two intermittently elastic webs.

Referring now to the figures, FIG. 1 illustrates schematically the various stages in the manufacture of a pair of elastic webs. A first longitudinally extending web (90) is provided having a first lateral edge (91), a second lateral edge (92) and an intermediate portion (93) located between the first and second lateral edges (91, 92). A first elastic element (94) is joined to the intermediate portion (93) of the first longitudinally extending web (90) by any method as known in the art. The first elastic element (94) as show is joined to the first web (90) in a longitudinally extending wave shape having wave crests (99) and wave troughs (100).

Further, a second elastic element (95) is joined to the first web (90) adjacent the first lateral edge (91). A third elastic element (96) is joined to the first web (90) adjacent the second lateral edge (92). These second and third elastic elements (95, 96) dramatically increase the functionality of the web. Controlling a web containing elastic elements may require additional equipment as compared to a web without elastic elements. By combining the first, second and third elastic elements (94, 95, 96) onto the same web, only a single web need be controlled with additional equipment.

Alternatively, if three webs contained the three separate elastic elements, three webs would need additional equipment.

A second web (97) may be placed on top of the first web and joined thereto. The second web (97) may have a width equal to the first web (90) alternatively, the second web (97) may have a width that is larger than or smaller than the width of the first web (90). A portion or portions of the first web (90) may be folded over a portion of the second web (97), alternatively a portion or portions of the second web (97) may be folded over a portion of the first web (90)

In FIG. 1, the first elastic element (94) is joined to the first web (90) in a regular sinusoidal configuration that has a relatively small amplitude. The first elastic element (94) may be laid-out in other undulating configurations, e.g. rectilinear wave configurations. The wave shape may be regular, with uniform wavelengths, or irregular with varying wavelengths. The wave shape may have uniform amplitude along its length; alternatively, the wave shape may have an amplitude that varies from one wave crest (99) or wave trough (100) to another.

Figure 1A:
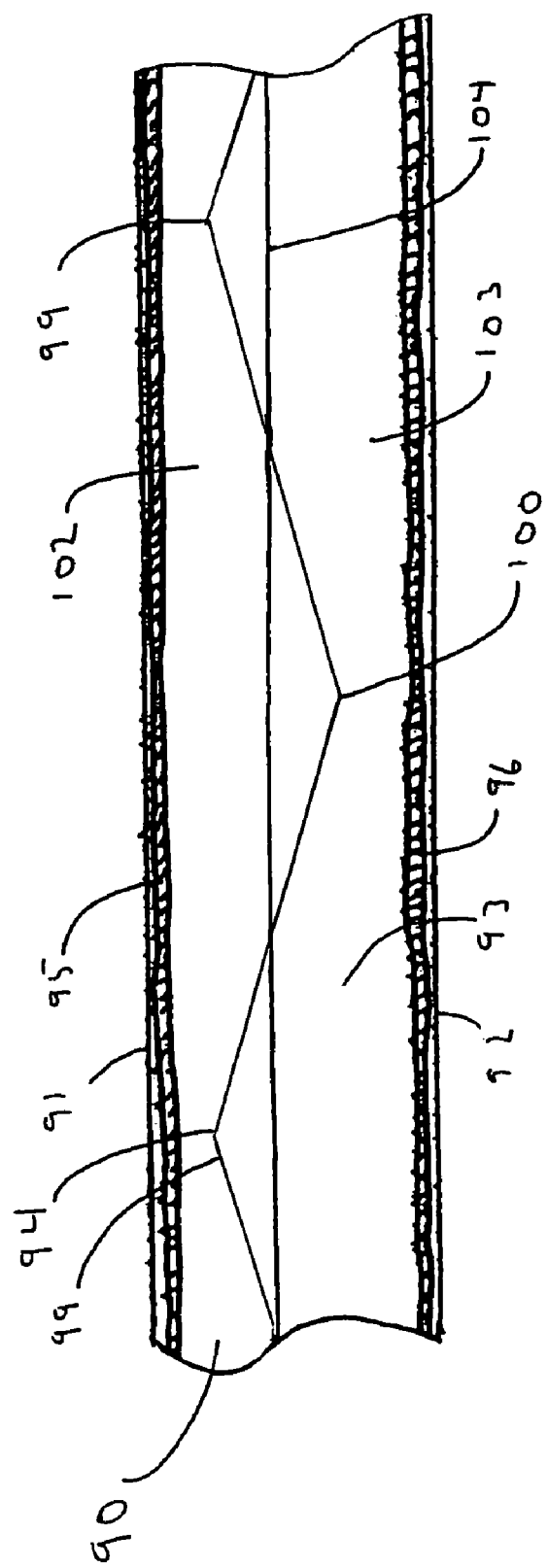
FIG. 1A illustrates a second version of two intermittently elastic webs.
Figure 1B:
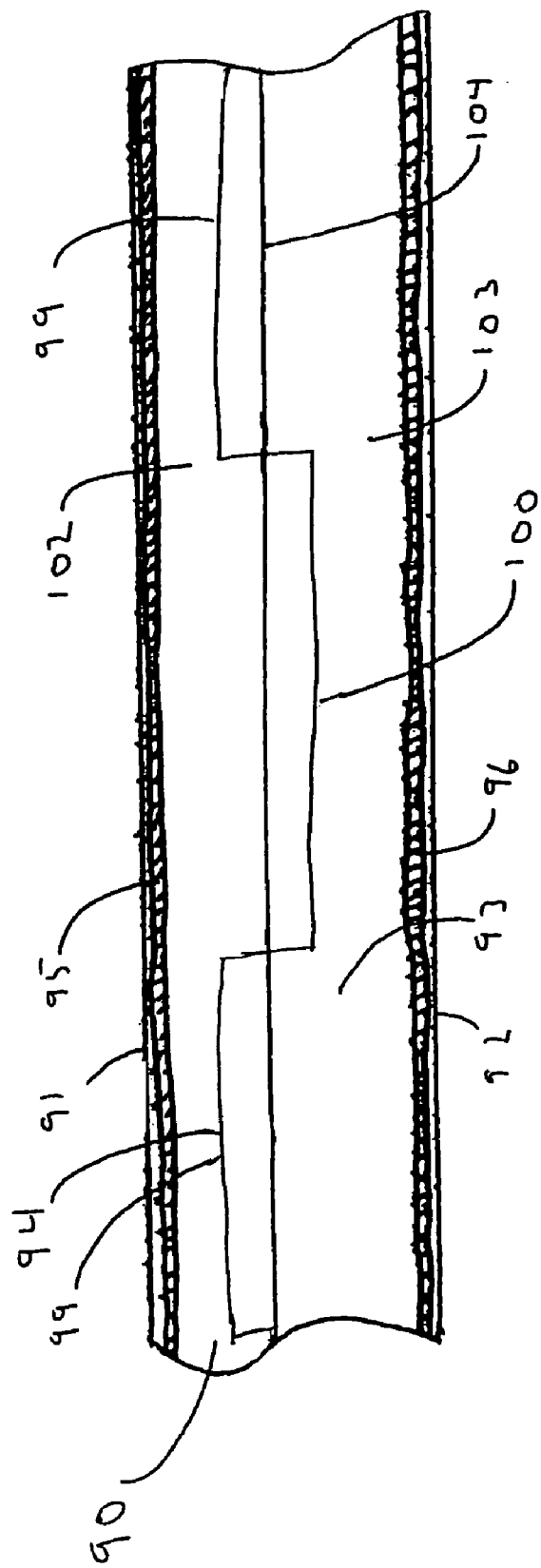
FIG. 1B illustrates a third version of two intermittently elastic webs.
Figure 1C:
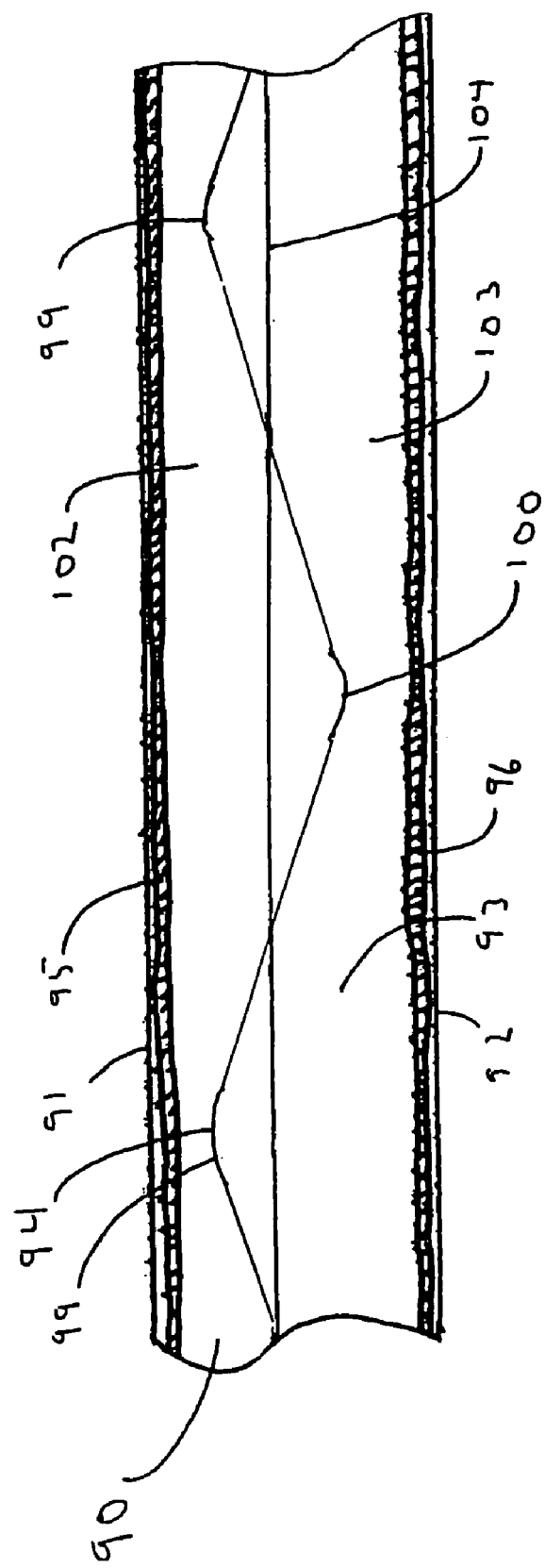
FIG. 1C illustrates a fourth version of two intermittently elastic webs.

FIGS. 1A, 1B, 1C and 1D illustrate the first elastic element (94) joined to the first web (90) in alternative wave shapes. Specifically FIG. 1A illustrates the first elastic element (94) joined in a liner wave shape. The first elastic element (94) joined in straight lines from the wave crest (99) to the wave trough (100) forming angles at the crest (99) and trough (100). FIG. 1B illustrates the first elastic element (94) joined to the first web (90) in a rectilinear wave shape. FIG. 1C illustrates the first elastic element (94) joined to the fire web (90) in a curvilinear shape.

Figure 1D:
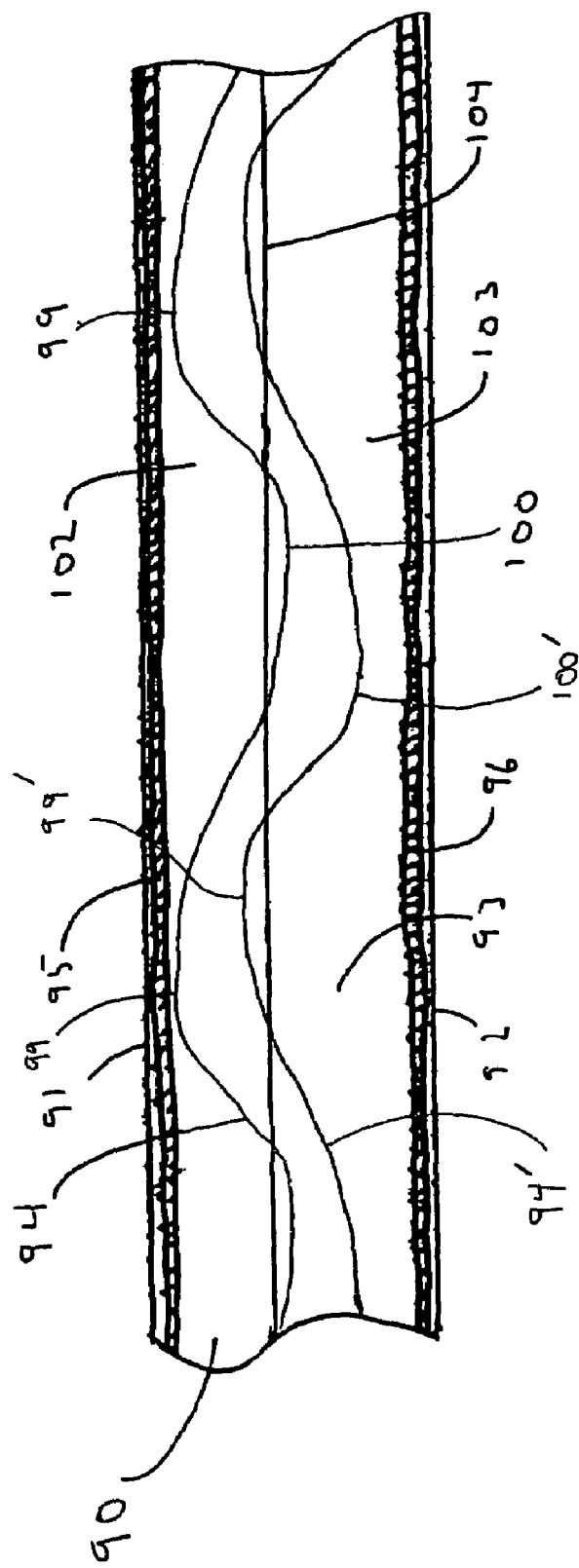
FIG. 1D illustrates a fifth version of two intermittently elastic webs.

FIG. 1D illustrates the first elastic element (94) joined to the first web and an additional first elastic element (94'), where the first elastic element (94) is generally closer to the first lateral edge (91) than the additional first elastic element (94'). The additional first elastic element (94') may have wave crests (99') and wave troughs (100') which align with the wave crests (99) and wave troughs (100) of the first elastic element (94), alternatively, the additional first elastic element (94') may have wave crests (99') and wave troughs (100') which for not align with the wave crests (99) and waive troughs (100) of the first elastic element (94) as shown in FIG. 1D.

The first web (90) may suitably be composed of a material which is either liquid permeable or liquid impermeable. The first web (90) may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The first web (90) may also be manufactured from a thin plastic film or other flexible liquid-impermeable material. For example, the first web (90) may be formed from a polyethylene film having a thickness of from about 0.013 millimeter (0.5 mil) to about 0.051 millimeter (2.0 mils). The materials of the first web (90) can be thermally or adhesively laminated together. If it is desired to present the first web (90) with a more clothlike feeling, the first web (90) may be formed from a polyolefin film having a nonwoven web laminated to the exterior surface thereof, such as a spunbond web of polyolefin fibers. The first web (90) may include bicomponent fibers such as polyethylene/polypropylene bicomponent fibers. Methods of forming such clothlike webs are known to those skilled in the art.

The first web (90) may be formed of a woven or non-woven fibrous web layer which has been totally or partially constructed or treated to impart a desired level of hydrophobicity or hydrophilicity. Still further, the first web (90) may optionally be composed of a micro-porous "breathable" material which permits vapors to escape while still preventing liquid from passing through the first web (90). For example, the first web (90) may include a vapor permeable non-woven facing layer laminated to a micro-porous film. The first web (90) can also be embossed or otherwise provided with a matte finish to provide a more aesthetically pleasing appearance.

The second web (97) may be composed from any material that is suitable for the first web (90) as described above. The second web (97) may be composed of a material that is similar to the first web (90); alternatively, the second web (97) may be composed of a material that is different than the first web (90).

Materials suitable for use as the first, second and third elastic elements (94, 95, 96) are well known to those skilled in the art. As is well known to those skilled in the art, suitable elastic materials include sheets, strands or ribbons of natural rubber, synthetic rubber, or thermoplastic elastomeric polymers. Exemplary examples of such materials are sheets or strands or ribbons of a polymeric, elastomeric material that may be adhered to the first web (90) in a stretched position, or that may be attached to the first web (90) while the first web (90) is pleated, such that elastic constrictive forces are imparted to the first web (90).

The first, second and third elastic elements (94, 95, 96) may be made of a latent elastic material which can be activated manufacture. The use of such a latent elastic material eliminates the need to maintain the first web (90) in a tensioned condition as the intermittently elastic webs (102, 103) are manufactured. Suitable latent elastic materials are known to those skilled in the art. For example, suitable latent elastic materials are commercially available from Exxon under the trade designation EXX601. Alternative latent elastic materials are described in WO98/29251 published Jul. 9, 1998 and entitled "A PROCESS FOR PRODUCING DIMENSIONALLY STABLE AND OR LATENT ELASTIC LAMINATE", the disclosure of which is hereby incorporated by reference.

The latent elastic material may be activated by a variety of methods known to those skilled in the art. For example, the latent elastic material may be activated by heating the diaper after it is manufactured to cause the material to retract.

The first, second and third elastic elements (94, 95, 96) may be composed from similar materials; alternatively, they may be composed from dissimilar materials. The first, second or third elastic element (94, 95, 96) may be composed of a single elastic strand, sheet or ribbon, or the element (94, 95, 96) may be composed of a plurality of elastic strands, sheets or ribbons, or combinations of the above.

Methods for joining the first, second and third elastic elements (94, 95, 96) to the first web (90) are known to those skilled in the art. Suitable methods include heat sealing, sonic bonding, adhesive bonding, stitching, and the like. The elastic elements (94, 95, 96) may be joined to the first web (90) utilizing a single method, all joined using adhesive. Alternatively, the elastic elements (94, 95, 96) may be joined to the first web (90) utilizing multiple methods, for example, the first elastic element (94) using adhesive, the second and third elastic elements (95, 96) utilizing heat sealing. The elastic elements (94, 95, 96) may be joined along there entire length to the first web (90), alternatively the elastic elements (94, 95, 96) may be joined intermittently along their length to the first web (90). The elastic elements (94, 95, 96) may be secured by joining the first web (90) to the second web (97). Alternatively, the elastic elements (94, 95, 96) may be joined directly to the first web (90). The elastic elements (95, 95, 96) may be joined to the first web (90) under the same elongation, or under different elongations. Any elastic element may be joined to the first web (90) under zero elongation; alternatively, elongated to 100 percent of its original length; alternatively elongated to 200 percent of its original length; alternatively, 300 percent of its original length.

A pair of intermittently elastic webs is produced by dividing the first web (90) carrying the elastic elements (94, 95, 96) into a first intermittently elastic web (102) and a second intermittently elastic web (103) by means of a longitudinally extending cut (104), which cuts the first elastic element (94) at those points at between wave crests and wave troughs.

For illustrative purposes, FIGS. 1, 1A, 1B, 1C, 1D and 2 illustrate a first intermittently elastic web (102) and a second intermittently elastic web (103) even though the first intermittently elastic web (102) and the second intermittently elastic web (103) do not exist until the first web (90) is cut.

The resultant first intermittently elastic web (102) is intermittently elastic because it includes cut portions of the first elastic element (94) located on the first lateral edge (91) side of the longitudinally extending cut (104). Correspondingly the second intermittently elastic web (103) is intermittently elastic because it includes cut portions of the first elastic element (94) located on the second lateral edge (92) side of the longitudinally extending cut (104). Each intermittently elastic web (102, 103) may have equal portions of the first elastic element (94); alternatively, each intermittently elastic web (102, 103) may have unequal portions of the first elastic element (94). Further, when an additional first elastic element (94') is present, each intermittently elastic web (102, 103) may have equal portions of the additional first elastic element (94'); alternatively, each intermittently elastic web (102, 103) may have unequal portions of the additional first elastic element (94'). For example, as illustrated in FIG. 1D the first intermittently elastic web (102) may contain 70% of the first elastic element (94) and 30% of the additional first elastic element (94'), and the second intermittently elastic web (103) may contain 30% of the first elastic element (94) and 70% of the additional first elastic element (94').

Figure 2:
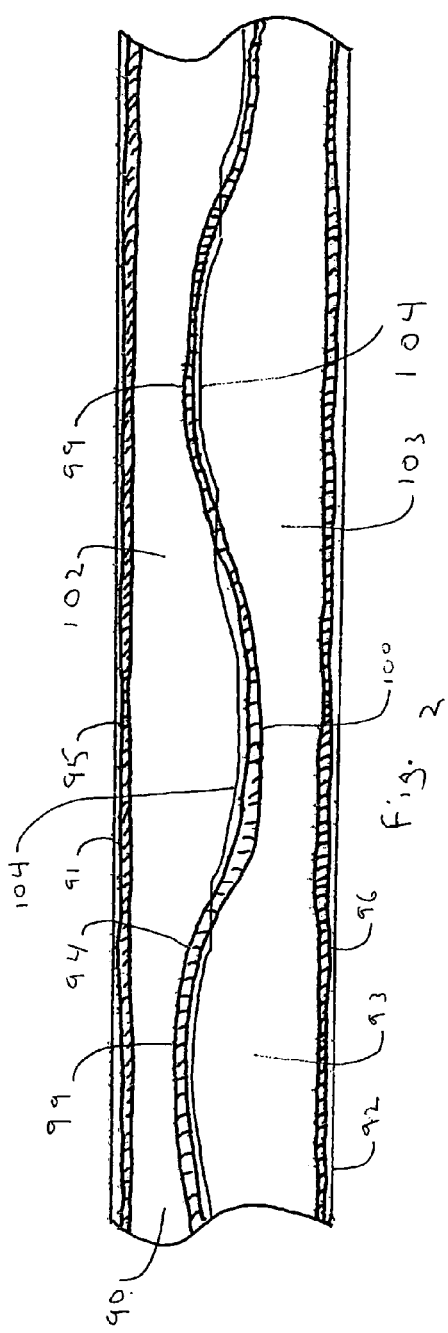
FIG. 2 illustrates a sixth version of two intermittently elastic webs.

The longitudinally extending cut (104) may be linear, curved, rectilinear, curvilinear or otherwise shaped. FIG. 1 illustrates a linear longitudinally extending cut (104). FIG. 2 illustrates a longitudinally extending cut (104) that generally follow the elastic strand along the wave crest (99) and wave trough (100), crossing over and cutting the first elastic element (94) at those points between wave crests and wave troughs. For particular application, the longitudinally extending cut (104) may stay within 30 mm of the first elastic element (94); alternatively, within 20 mm of the first elastic element (94); alternatively, within 10 mm of the first elastic element (94).

Portions of the intermittently elastic web (102, 103) may be removed during or after the longitudinally extending cut (104) is made. For example, portions (115) of the intermittently elastic web (102, 103) located between the first elastic element (94) and a cut edge (107, 108) may be removed using any method as known in the art. Further, when an additional first elastic element (94') is present, portions of the intermittently elastic web (102, 103) located between the additional first elastic element (94') and a cut edge (107, 108) may be removed.

Figure 3:
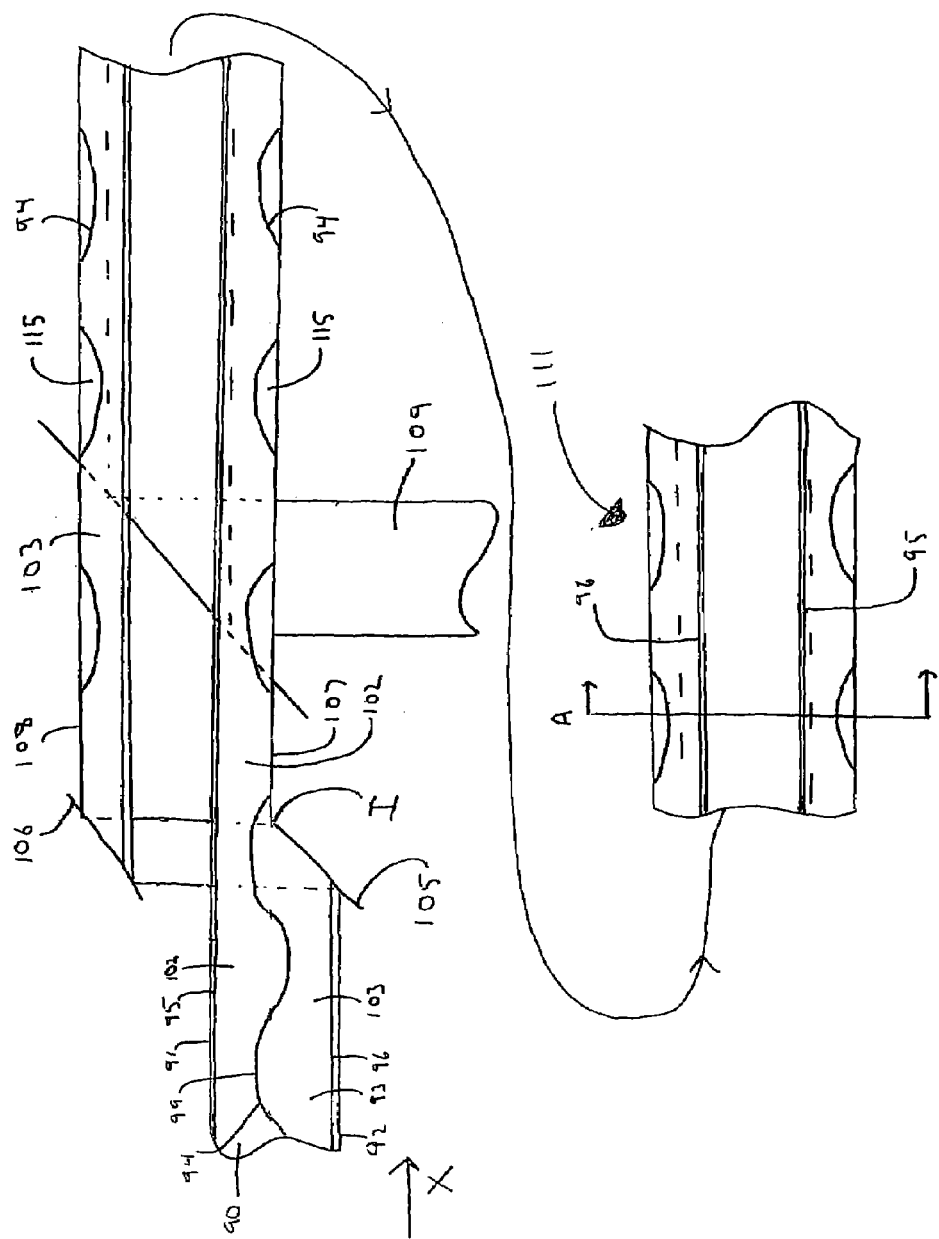
FIG. 3 illustrates schematically the various stages of fastening intermittently elastic webs to a third web.

FIG. 3 is a schematic illustration of how the described method can be applied as a part of a more elaborate process. Those components shown in FIG. 3 that find correspondence with components in the FIG. 1 illustration have been identified by the same reference numerals. A first web (90) containing a sinusoidal shaped first elastic element (94) and second and third elastic elements (95, 96) is advanced in the direction marked X in FIG. 3. When the first web (90) reaches a cutting device (indicated at position "I"), the web is cut along its longitudinal axis into first and second intermittently elastic webs (102, 103), the first (102) including a wave crest (99) and the second (103) including a wave trough (100). The wave crest (99) and the wave trough (100) are displaced longitudinally relative to one another through one-half wavelength at the location I, i.e. in the web movement direction such that the wave crest (99) and wave troughs (100) are substantially aligned in the longitudinal direction. This is accomplished by passing the second intermittently elastic web (103) over a pair of turn bars (105, 106). Any suitable alternative method as known in the art may be utilized.

The pair of turn bars (105, 106) also reorients the intermittently elastic webs (102, 103) such that the first and second lateral edges (91, 92) are in closer proximity to one another than the cut edges (107, 108). Any suitable method as known in the art may be utilized, for example the intermittently elastic webs (102, 103) may be displaced laterally in relationship to each other; alternatively, the intermittently elastic webs (102, 103) may be rotated about respective longitudinal axes.

After the second intermittently elastic web (103) has left the second turn bar (106), it moves in the direction parallel with the first intermittently elastic web (102) and in spaced relationship therewith.

The parallel moving first and second intermittently elastic webs (102, 103) may then joined to a third web (109) forming a composite web (111). The third web (109) may enter the process by turn bar (107) or any other suitable means. The first intermittently elastic web (102) is joined to the third web (109) at a location between the portions of the first elastic element (94) and the second elastic element (95). Accordingly the second intermittently elastic web is joined to the third web (109) at a location between the portions of first elastic element (94) and the third elastic element (96). The intermittently elastic webs (102, 103) may be joined to the third web (109) with any method as known in the art, e.g. by ultrasound welding or adhesive. The webs (102, 103, 109) may be joined continuously; alternatively, they may be joined intermittently.

As shown, the longitudinal length of the first and second intermittently elastic webs (102, 103) is similar to the longitudinal length of the third web (109). Alternatively, either the first and second intermittently elastic webs (102, 103) or the third web (109) may be applied with a cut and place module. In this way, the longitudinal length of the first and second intermittently elastic webs (102, 103) may be either longer or shorter than the longitudinal length of the third web (109).

Figure 4:
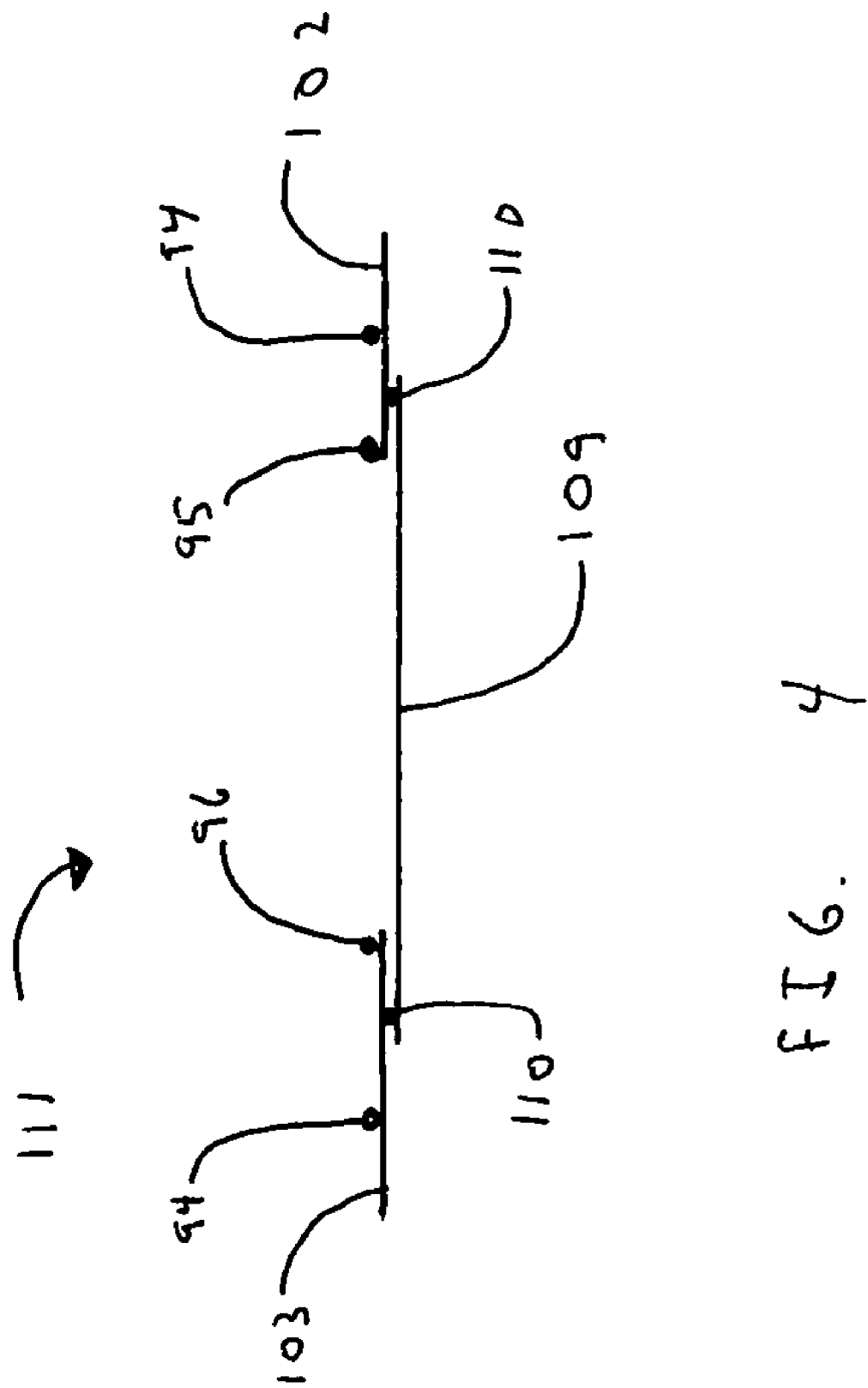
FIG. 4 illustrates a cross-sectional view of FIG. 3 as viewed at A-A.

FIG. 4 illustrates a cross-sectional view of FIG. 3 as viewed at A-A showing the relative positioning of the intermittently elastic webs (102, 103), the portions of the first elastic element (94), the second and third elastic elements (95, 96) and the third web (109). Also shown are adhesive beads (110) illustrating the location where the first and second intermittently elastic webs (102, 103) are joined to the third web (109), specifically, at a location between portions of the first elastic element (94) and the second elastic element (95).

The third web (109) may be a single layer or material. Alternatively the third web (109) may be a multi-layer structure, for example a structure comprising a liquid-impervious outer cover, a liquid pervious liner, and an absorbent core medium therebetween. Where the third web (109) is a single layer of material, it may suitably be composed of a material which is either liquid permeable or liquid impermeable. The third web (109) may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The third web (109) may be a nonwoven material. The third web (109) may also be manufactured from a thin plastic film or other flexible liquid-impermeable material. For example, the third web (109) may be formed from a polyethylene film having a thickness of from about 0.013 millimeter (0.5 mil) to about 0.051 millimeter (2.0 mils). The materials of the third web (109) can be thermally or adhesively laminated together. If it is desired to present the third web (109) with a more clothlike feeling, the third web (109) may be formed from a polyolefin film having a nonwoven web laminated to the exterior surface thereof, such as a spunbond web of polyolefin fibers. The third web (109) may include bicomponent fibers such as polyethylene/polypropylene bicomponent fibers. Methods of forming such clothlike webs are known to those skilled in the art.

Representative Absorbent Article

Figure 5:
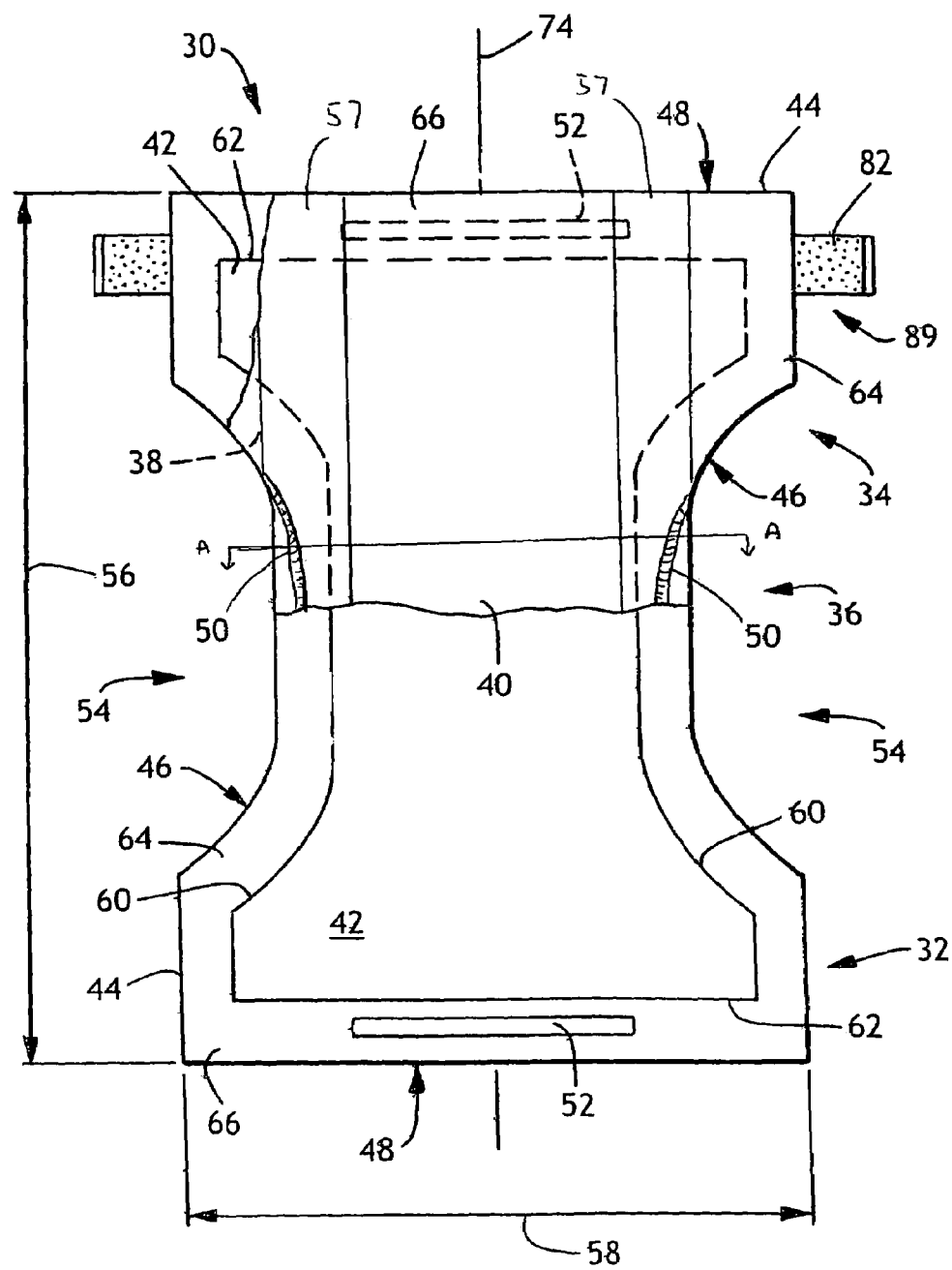
FIG. 5 illustrates a plan view of a disposable absorbent article in an unfolded, flat-out, uncontracted state (i.e., with all elastic induced gathering and contraction removed), with the bodyfacing surface of the article facing the viewer and with portions of the article partially cut away to illustrate underlying features.

FIG. 5 illustrates a disposable absorbent article such as a disposable diaper (30) in an unfolded, flat-out, uncontracted state (i.e., with all elastic induced gathering and contraction removed). Portions of the structure are partially cut away to more clearly show the interior construction of the diaper (30), with the surface of the diaper (30) which contacts the wearer facing the viewer. FIGS. 5 and 6 illustrate a disposable diaper (30) as having a front region (32), a rear region (34) and a crotch portion (36) located between the front and rear regions. The diaper (30) comprises a backsheet (38), a topsheet (40), and an absorbent core (42) situated between the backsheet and the topsheet. The outer edges of the diaper (30) define a periphery (44) with transversely opposed, longitudinally extending side edges (46); longitudinally opposed, transversely extending end edges (48); and a system of elastomeric gathering members, such as a system including leg elastics (50) and waist elastics (52). The longitudinal side edges (46) define the leg openings (54) for the diaper (30), and optionally, are curvilinear and contoured. The transverse end edges (48) are illustrated as straight, but optionally, may be curvilinear. The diaper (30) may also comprise additional components to assist in the acquisition, distribution and storage of bodily waste. For example, the diaper (30) may comprise a transport layer, such as described in U.S. Pat. No. 4,798,603, issued to Meyer et al., or a surge management layer, such as described in European Patent Application Publication No. 0 539 703, published May 5, 1993.

The diaper (30) generally defines a longitudinally extending length dimension (56), and a laterally extending width dimension (58), as representatively illustrated in FIG. 5. The diaper (30) may have any desired shape, such as rectangular, I-shaped, a generally hourglass shape, or a T-shape.

The backsheet (38) defines a length and a width which, in the illustrated version, coincide with the length and width of the diaper (30). The absorbent core (42) generally defines a length and width which are less than the length and width of the backsheet (38), respectively. Thus, marginal portions of the diaper (30), such as marginal sections of the backsheet (38), may extend past the transversely opposed, longitudinally extending terminal side edges (60) and/or the longitudinally opposed, transversely extending terminal end edges (62) of the absorbent core (42) to form side margins (64) and end margins (66) of the diaper (30). The topsheet (40) is generally coextensive with the backsheet (38), but may optionally cover an area which is larger or smaller than the area of the backsheet, as desired. The backsheet (38) and topsheet (40) are intended to face the garment and body of the wearer, respectively, while in use. As used herein when describing the topsheet (40) in relation to the backsheet (38) and vice versa, the term "associated" encompasses configurations in which the topsheet is directly joined to the backsheet, and configurations where the topsheet is indirectly joined to the backsheet by affixing portions of the topsheet to intermediate members which in turn are affixed to at least portions of the backsheet. The topsheet (40) and the backsheet (38) can, for example, be joined to each other in at least a portion of the diaper periphery (44) by attachment mechanisms (not shown) such as adhesive bonds, sonic bonds, thermal bonds, pinning, stitching, or a variety of other attachment techniques known in the art, as well as combinations thereof.

The topsheet (40) suitably presents a bodyfacing surface which is compliant, soft feeling, and non-irritating to the wearer's skin. Further, the topsheet (40) may be less hydrophilic than the absorbent core (42), to present a relatively dry surface to the wearer, and is sufficiently porous to be liquid permeable, permitting liquid to readily penetrate through its thickness. The topsheet (40) is suitably employed to help isolate the wearer's skin from liquids held in the absorbent core (42). Various woven and nonwoven fabrics may be used for the topsheet (40). The topsheet (40) may be composed of a substantially hydrophobic material, and the hydrophobic material may, optionally, be treated with a surfactant, or otherwise processed, to impart a desired level of wettability and hydrophilicity. Specifically, the topsheet (40) may be a nonwoven, spunbond, polypropylene fabric composed of about 2.8 to about 3.2 denier fibers formed into a web having a basis weight of about 22 gsm and a density of about 0.06 g/cc.

The backsheet (38) may suitably be composed of a material which is either liquid permeable or liquid impermeable. It is generally desirable that the backsheet (38) be formed from a material which is substantially liquid impermeable. For example, a typical backsheet (38) can be manufactured from a thin plastic film or other flexible liquid impermeable material. Moreover, the backsheet (38) may be formed from a polyethylene film having a thickness of from about 0.012 mm (0.5 mil) to about 0.051 mm (2.0 mils). If desirous of presenting the backsheet (38) with a more cloth-like feel, the backsheet may comprise a polyethylene film having laminated to the lower or opposing surface thereof a nonwoven web, such as a spunbond web of polyolefin fibers. Methods of forming such cloth-like outer covers are known to those skilled in the art. Further the backsheet (38) may be a stretchable material, a method of forming such a material may be found in U.S. Pat. No. 5,226,992 issued to Morman, further various examples of extensible materials are described in U.S. Pat. No. 6,264,641 issued to VanGompel et al.; the entire disclosures of which are hereby incorporated by reference in a manner that is consistent herewith. The backsheet (38) may optionally be composed of micro-porous "breathable" material which permits vapors to escape from the absorbent core (42) while still preventing liquid exudates from passing through the backsheet.

The absorbent core (42) may comprise a matrix of hydrophilic fibers, such as a web of cellulosic fluff, mixed with particles of a high-absorbency material commonly known as superabsorbent material. In a particular version, the absorbent core (42) comprises a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed. The high-absorbency material can be selected from natural, synthetic and modified natural polymers and materials.

The absorbent core (42) may have any of a number of shapes. For example, the absorbent core (42) may be rectangular, I-shaped or T-shaped. It is often considered as desirable for the absorbent core (42) to be narrower in the crotch portion than the rear or front region(s).

Figure 5A:
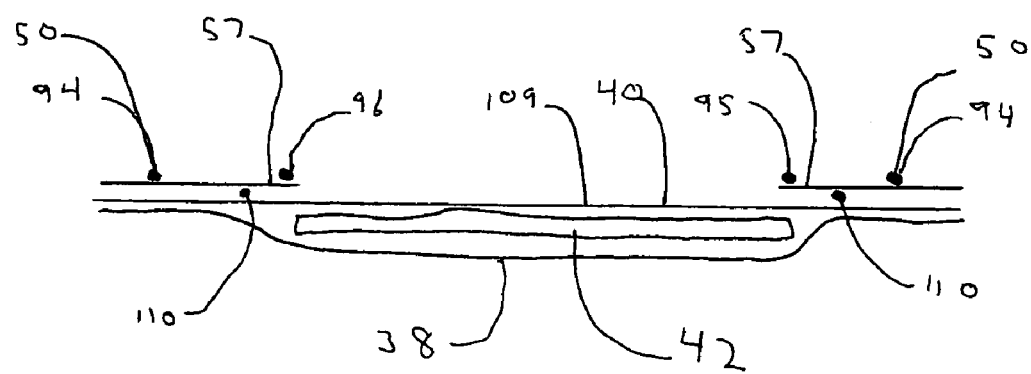
FIG. 5A illustrates a cross-sectional view of FIG. 5 as viewed at A-A.

As representatively illustrated in FIG. 5, the diaper (30) may include a pair of containment flaps (57) that are configured to provide a barrier to the lateral flow of body exudates. The containment flaps (57) may be located along the longitudinally extending side edges (46) of the diaper (30) adjacent the side edges of the absorbent core (42). Each containment flap (57) typically defines an unattached edge that is configured to maintain an upright, perpendicular configuration in at least the crotch portion (36) of the diaper (30) to form a seal against the wearer's body. The containment flaps (57) may extend longitudinally along the entire length of the absorbent core (42) or may only extend partially along the length of the absorbent core (42). When the containment flaps (57) are shorter in length than the absorbent core (42), the containment flaps (57) can be selectively positioned anywhere along the side edges (46) of the diaper (30) in the crotch portion (36). The containment flaps (57) extend along the entire length of the absorbent core (42) to better contain the body exudates. The combination of the containment flaps (57) and leg elastics (50) may be constructed of the intermittently elastic webs (102, 103) of the present invention. FIG. 5A illustrates a cross-sectional view of the diaper (30) of FIG. 5 as viewed at A-A.

The disposable absorbent articles described herein also comprise fasteners (82) for securing the absorbent article about the waist of the wearer. The illustrated versions of the diaper (30) comprise such fasteners (82). In at least one version, the fasteners (82) are situated in the rear region (34) of the diaper (30), and located inboard each longitudinal extending side edge (46). The fasteners (82) may be configured to encircle the hips of the wearer and engage the backsheet (38) of the front region (32) of the diaper (30) for holding the diaper (30) on the wearer. Suitable fasteners are well known to those of skill. Desirably, the fasteners (82) are releasably engageable directly with the garment facing surface of the backsheet (38). Desirably, the fasteners (82) comprise a mechanical fastening system. Alternatively, the diaper (30) may comprise a fastening panel (68) situated in the front region (32) of the garment facing surface of the backsheet (38). In such a configuration, the fasteners (82) are releasably engageable with the fastening panel (68) to maintain the diaper (30) about the waist of the wearer. Such an arrangement provides the ability to vary the size of the waist opening in very small increments over a wide range to fit the waist of the wearer. The fasteners (82) may have a variety of shapes and sizes which provide the desired fastening of the diaper (30) about the waist of the wearer.

In disposable absorbent articles utilizing the present invention, the fasteners (82) may be joined to the intermittently elastic webs (102, 103), as shown in FIG. 7. The fasteners (82) may be joined to the intermittently elastic webs (102, 103) at any place in the process, before the first elastic element (94) is joined to the first web (90), prior to, or after cutting the web into a pair of intermittently elastic webs (102, 103) or after joining the intermittently elastic webs (102, 103) to the disposable absorbent article. In this way, a portion of the intermittently elastic webs (102, 103) forms the ears (89) of the diaper (30). FIG. 7 utilizes the intermittently elastic webs (102, 103) cut as illustrated in FIG. 2.

As shown in FIGS. 5 and 6, for example, the mechanical fastening system may be a hook-and-loop type of fastening system. Such fastening systems typically comprise engagement members having the form of a "hook" or hook-like, male component, and comprise a cooperating "loop" or loop-like, female component, which engages and releasably interconnects with the hook component. Desirably, the interconnection is selectively releasable and re-attachable. Conventional systems are, for example, available under the VELCRO trademark.

A configuration which employs a selectively releasable, inter-engaging mechanical fastening system can, for example, locate the first fastener component on the ear (89), and can locate the cooperating, second fastener component on the fastening panel (68). For example, with the representatively shown hook-and-loop fastener, the fastening component, which is attached to the ear (89), may comprise a hook type of mechanical engagement element, and the complementary fastening component, is the fastening panel (68) which can comprise a loop type of fastening element.

The method of the present invention may provide several benefits including increased processability and reduced waist. Further, disposable absorbent articles produced with the method of the present invention may display improved fit and improved performance.

It will be appreciated that details of the method of the invention, given for purposes of illustration, are not to be construed as limiting the scope of this invention. Although only a few exemplary aspects of this invention have been described in detail above, those skilled in the art will readily appreciate that many modifications are possible in the exemplary aspects without materially departing from the novel teachings and advantages of this invention. Accordingly, all such modifications are intended to be included within the scope of this invention, which is defined in the following claims and all equivalents thereto. Further, it is recognized that many aspects may be conceived that do not achieve all of the advantages of some aspects, particularly of the preferred aspects, yet the absence of a particular advantage should not be construed to necessarily mean that such an aspect is outside the scope of the present invention.

What is claimed is:

1. A method of producing an intermittently elastic web comprising:
   providing a first longitudinally extending web having a first lateral edge, a second lateral edge and an intermediate portion located between the first and second lateral edges;

joining a first elastic element to the intermediate portion in a longitudinally extending wave shape, the wave shape having wave crests and wave troughs;

joining a second elastic element to the first longitudinally extending web adjacent the first lateral edge;

joining a third elastic element to the first longitudinally extending web adjacent the second lateral edge; and cutting the web longitudinally to form a first and second intermittently elastic web comprising cut portions of the first elastic element.

2. The method of claim 1 wherein the first elastic element is extended at least 100 percent prior to joining to the intermediate portion.

3. The method of claim 1 wherein the first elastic element is joined in a regular wave shape.

4. The method of claim 1 wherein the first elastic element is joined in a rectilinear wave shape.

5. The method of claim 1 wherein the cutting the web longitudinally comprises a curvilinear cut.

6. The method of claim 1 wherein each intermittently elastic web comprises a substantially equal portion of the first elastic element.

7. The method of claim 1 wherein the cut edge is within 20 mm of the portion of the first elastic element.

8. The method of claim 1 wherein the second and third elastic elements are intermittently attached adjacent to the lateral edges.

9. The method of claim 1 further comprising joining a second web to the first web such that the first elastic element is contained between the first web and the second web.

10. The method of claim 9 wherein the first web and the second web are nonwovens.

11. The method of claim 9 wherein the either the first web or the second web is a film.

12. The method of claim 1 further comprising:
displacing the first and second intermittently elastic webs longitudinally in relation to each other so that the wave crests and wave troughs are substantially aligned in the longitudinal direction; and reorienting the first and second intermittently elastic webs such that the two lateral edges are in closer proximity to one another than the two cut edges.

13. The method of claim 12 wherein the reorienting the first and second intermittently elastic webs comprises displacing the first and second intermittently elastic webs laterally in relation to each other.

14. The method of claim 12 wherein the reorienting the first and second intermittently elastic webs comprises rotating the first and second intermittently elastic webs about a longitudinal axis.

15. The method of claim 12 further comprising:
joining the first intermittently elastic web to a third web at a location between the cut portions of the first elastic element and the second elastic element; and joining the second intermittently elastic web to the third web at a location between the cut portions of the first elastic element and the third elastic element.

16. The method of claim 1 further comprising removing portions of the first and second intermittently elastic web located between the cut portions of the first elastic element and the cut edge.

17. A method of producing a disposable absorbent article comprising:
providing an absorbent assembly comprising a liquid-impervious outer cover, a liquid pervious liner, and an absorbent core therebetween;

providing a first longitudinally extending web having a first lateral edge, a second lateral edge and an intermediate portion located between the first and second lateral edges;

joining a first elastic element to the intermediate portion in a longitudinally extending wave shape, the wave shape having wave crests and wave troughs;

joining a second elastic element to the first longitudinally extending web adjacent the first lateral edge;

joining a third elastic element to the first longitudinally extending web adjacent the second lateral edge;

cutting the web longitudinally to form a first and second intermittently elastic webs comprising cut portions of the first elastic element;

displacing the first and second intermittently elastic webs longitudinally in relation to each other so that the wave crests and wave troughs are substantially aligned in the longitudinal direction;

joining the first intermittently elastic webs to the absorbent assembly, the first intermittently elastic webs joined at a location between the cut portions of the first elastic element and the second elastic element; and joining the second intermittently elastic webs to the absorbent assembly, the second intermittently elastic webs joined at a location between the cut portions of the first elastic element and the third elastic element.

18. The method of claim 17 wherein the absorbent assembly is a portion of a continuous web.

19. The method of claim 17 further comprising joining a fastener to the intermittently elastic webs.

20. A method of producing a disposable absorbent article comprising:
providing an absorbent assembly comprising a liquid-impervious outer cover, a liquid pervious liner, and an absorbent core therebetween;

providing a first longitudinally extending web having a first lateral edge, a second lateral edge and an intermediate portion located between the first and second lateral edges;

joining a first elastic element to the intermediate portion in a longitudinally extending wave shape, the wave shape having wave crests and wave troughs;

joining a second elastic element to the first longitudinally extending web adjacent the first lateral edge;

joining a third elastic element to the first longitudinally extending web adjacent the second lateral edge;

cutting the web longitudinally to form a first and second intermittently elastic webs comprising cut portions of the first elastic element and a cut edge;

removing portions of the first and second intermittently elastic web located between the cut portions of the first elastic element and the cut edge;

displacing the first and second intermittently elastic webs longitudinally in relation to each other so that the wave crests and wave troughs are substantially aligned in the longitudinal direction;

joining the first intermittently elastic webs to the absorbent assembly at a location between the cut portions of the first elastic element and the second elastic element; and joining the second intermittently elastic web to the absorbent assembly at a location between the cut portions of the first elastic element and the third elastic element.

* * * * *